United States Patent [19]

Jarreau et al.

[11] 4,330,544
[45] May 18, 1982

[54] AMINO-ALKOXY PYRAZOLES AND PHARMACEUTICAL COMPOSITIONS

[75] Inventors: François-Xavier Jarreau, Versailles; Jean J. Koenig, Vernou La Celle, both of France

[73] Assignee: Etablissements Nativelle S.A., Paris, France

[21] Appl. No.: 250,952

[22] Filed: Apr. 1, 1981

[30] Foreign Application Priority Data

Apr. 1, 1980 [FR] France .................. 80 07301

[51] Int. Cl.³ .............. A61K 31/535; A61K 31/415; C07D 413/12; C07D 231/20
[52] U.S. Cl. ..................... 424/248.56; 424/250; 424/251; 424/267; 424/272; 424/273 P; 544/140; 544/333; 544/371; 544/405; 546/205; 546/211; 548/235; 548/236; 548/300; 548/336; 548/348; 548/376; 548/374; 260/245.6
[58] Field of Search ........... 544/140, 371, 333, 405; 546/205, 211; 548/374, 376, 336, 235, 236, 348, 300; 260/245.6; 424/248.56, 250, 251, 267, 272, 273 P

[56] References Cited

FOREIGN PATENT DOCUMENTS 2167997  8/1973  France .

Primary Examiner—Robert W. Ramsuer

Attorney, Agent, or Firm—Sughrue, Mion, Zinn, Macpeak and Seas

[57] ABSTRACT

An aminoalkoxypyrazole of the general formula (I)

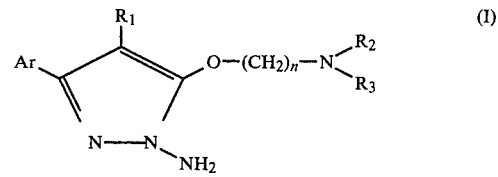

wherein Ar is a phenyl, benzyl or naphthyl group, or a phenyl group substituted by one or more halogen atoms, or by one or more alkyl, cyano, nitro, hydroxy or alkoxy groups; $R_1$ is a hydrogen atom or an alkyl group; $R_2$ and $R_3$, which may be the same or different, are a hydrogen atom or an alkyl group, or form, with the nitrogen atom to which they are attached, a 5- to 7-membered heterocyclic ring; n is an integer of from 1 to 4; as well as the mineral or organic acid salts thereof. A further embodiment of the invention is the application of the derivatives of the general formula (I) as medications, in particular, for the treatment of depression, polyfunctional disorders, migraines and cardiovascular diseases.

8 Claims, No Drawings

AMINO-ALKOXY PYRAZOLES AND PHARMACEUTICAL COMPOSITIONS

FIELD OF THE INVENTION

The present invention, relates to new pyrazole derivatives, and in particular to aminoalkoxy pyrazoles, a process for their preparation and their therapeutic application.

BACKGROUND OF THE INVENTION

Pyrazole derivatives and pyrazolone are described in particular in French Pat. No. 2,167,997, to applicants. This French Patent relates in particular to compounds of the 1-amino pyrazole type, whose carbon atom at the 5-position is substituted by a hydroxy or lower alkoxy group, which possess interesting properties enabling their medicinal application.

SUMMARY OF THE INVENTION

As described above, the present invention relates to pyrazole derivatives comprising a functional alkoxy group substituted on the carbon atom at the 5-position of the pyrazolyl nucleus, which confers specific properties upon these compounds.

An embodiment of this invention provides derivatives of the amino-alkoxy pyrazole type represented by the general formula (I):

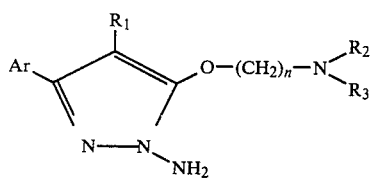 (I)

wherein Ar is a phenyl, benzyl or naphthyl group or a phenyl group substituted by one or more halogen atoms or by one or more alkyl, cyano, nitro, hydroxy or alkoxy groups; $R_1$ is a hydrogen atom or an alkyl group; $R_2$ and $R_3$, which may be the same or different, are a hydrogen atom or an alkyl group, or form, with the nitrogen atom to which they are attached, a 5- to 7-membered heterocyclic ring; n is an integer of from 1 to 4; as well as their salts with a mineral or organic acid.

A further embodiment of the invention is the application of the derivatives of the general formula (I) as medications, in particular, for the treatment of depression, polyfunctional disorders, migraines and cardiovascular diseases.

DETAILED DESCRIPTION OF THE INVENTION

In the general formula (I) shown above, Ar can be a phenyl group, or a benzyl, 1-naphthyl, 2-naphthyl group, or a substituted phenyl group, for example an o-, m- or p-chlorophenyl, 2,4-dichlorophenyl, 2,4,6-trichlorophenyl, p-hydroxyphenyl, p-methoxyphenyl, p-cyanophenyl, p-nitrophenyl or a tolyl group. $R_1$ is a hydrogen atom or an alkyl group such as methyl, ethyl, n-propyl, isopropyl, butyl, etc. $R_2$ and $R_3$, which may be the same or different, are a hydrogen atom or an alkyl group such as methyl, ethyl, n-propyl, or isopropyl; when $R_2$ and $R_3$ form, with the nitrogen atom to which they are attached, a 5- to 7-membered heterocyclic ring, this heterocyclic group can be a pyrrolyl, azepinyl, pyrrolidinyl, pyrrolinyl, or piperidyl group. This heterocyclic group may contain a second heteroatom such as a nitrogen or oxygen atom, and be, for example, an imidazolyl, pyrazolyl, pyrazinyl, pyrimidinyl, oxazolyl, imidazolinyl, pyrazolidinyl, pyrazolinyl, piperazinyl, 4-phenylpiperazinyl, or a morpholinyl group.

Among the derivatives of general formula (I), the invention preferably relates to those derivatives in which Ar is a phenyl group or is a phenyl group substituted by one or more chlorine atoms, and more especially a p-chlorophenyl group, $R_1$ is a hydrogen atom or a lower alkyl group, $R_2$ and $R_3$ are a hydrogen atom or a lower alkyl group, or form, together with the nitrogen atom to which they are attached, a piperazinyl, 4-(hydroxyethyl)piperazinyl, piperidyl, pyrrolidinyl, or a morpholinyl group, and n is 2 or 3.

The invention also relates to the salts of the derivatives of the general formula (I), and in particular to the pharmaceutically acceptable salts, obtained by action of common mineral or organic acids, such as hydrochloric, sulfuric, phosphoric, oxalic, lactic, citric acids, etc. These salts can be obtained using the processes conventional in the art.

The aminoalkoxy-pyrazoles of the invention, represented by the general formula (I) above, can be prepared from the corresponding amino-pyrazolones represented by the general formula (II):

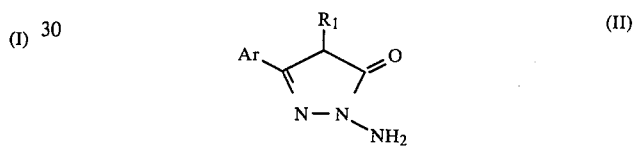 (II)

wherein Ar and $R_1$ have the definitions given above, by reaction with a haloalkylamine of the general formula (III):

 (III)

$$X-(CH_2)_n-NR_2R_3$$

wherein X is a halogen atom, n, $R_2$ and $R_3$ have the definitions given for the general formula (I), in the presence of a hydride, an amide or an alkali metal alcoholate in an organic solvent.

The aminopyrazolones of the general formula (II) can be prepared in accordance with the process described in French Pat. No. 2,167,997, by internal transposition in a derivative of 5-hydrazinoisoxazole, in the presence of an excess of anhydrous hydrazine.

The haloalkylamines of the general formula (III) used as reactants in accordance with the process of the invention are generally available commercially in the form of hydrochlorides. It is preferable to transform these hydrochlorides into the corresponding bases, at the time of use, by dissolving them in a saturated solution of potassium carbonate and extracting them with ether, using the method described in *Fieser Reagents* IV, page 267.

Examples of suitable haloalkylamines of the general formula (III) include chloroalkylamines in particular, such as N-(2-chloroethyl)-dimethylamine, N-(3-chloropropyl)dimethylamine, or N-(2-chloroethyl)-diisopropylamine, or an N-chloroalkylated heterocyclic ring, such as a 5- to 7-membered ring comprising, if desired, a second heteroatom such as a nitrogen or oxygen atom, substituted on the nitrogen atom by a chloroalkyl group, preferably N-(2-chloroethyl)-morpholine, N-(2-chloroethyl)-pyrrolidine, N-(3-chloropropyl)-piperidine, or N-(2-chloroethyl)-4-phenylpiperazine.

The starting aminopyrazolone, represented by the general formula (II), is preferably a 1-aminopyrazol-5-one such as 1-amino-3-(p-chlorophenyl)-pyrazolone, 1-amino-3-phenylpyrazolone, or 1-amino-3-phenyl-4-methylpyrazolone.

In accordance with the process of the invention, the reaction is preferably carried out in an organic solvent containing the starting amino pyrazolone, in the presence of a hydride or an alkali metal amide, to which is added progressively a chloroalkylamine of the general formula (III). For example, sodium or potassium hydride or sodium amide may be used.

The reaction is carried out at room temperature, but it may be preferable to bring the reaction medium to a temperature of between 20° and 100° C., and preferably between 50° and 80° C.

The reaction is carried out in an appropriate organic solvent, for example an aprotic solvent such as tetrahydrofuran, dimethylformamide, dimethyl sulfoxide, dioxane, diglyme, an alkyl ether, etc. When the base is an alkali metal alcoholate, it is preferable to use the corresponding alcohol as the solvent, for example, sodium methoxide in methanol.

The following examples are given to illustrate the invention in greater detail without limiting the scope thereof.

EXAMPLE 1

1-Amino-3-(p-chlorophenyl)-5-(morpholinoethoxy)-pyrazole

In a 1 l three-necked flask fitted with a condenser and a tube with calcium chloride, a nitrogen inlet, a run-off tube and an agitator, 3.05 g of 1-amino-3-(p-chlorophenyl)pyrazolone were placed in 200 ml of distilled dimethylformamide. Nitrogen was bubbled into the solution for 15 minutes, then it was cooled to approximately 0°–5° C. using an ice bath. 0.4 g of sodium hydride was added and it was maintained under agitation for 15 minutes, allowing the temperature to return to room temperature.

It was again cooled to 0°–5° C. using an ice bath, and 4.5 g of 2-chloro-N-ethylmorpholine was added dropwise under agitation. The mixture was allowed to react at room temperature, and the reaction progress was followed by thin-layer chromatography.

When the reaction was complete, the dimethylformamide was distilled off under reduced pressure (0.1 mm Hg approximately). The residue was dissolved in 300 ml of distilled water and, after washing with chloroform, the organic phases were extracted with an aqueous solution of 10% citric acid. It was rendered alkaline with sodium carbonate and extracted with diethyl ether. After washing with an aqueous solution saturated with sodium chloride, drying and evaporation under vacuum, 3.10 g of 1-amino-3-(p-chlorophenyl)-5-(morpholinoethoxy)-pyrazole was obtained, in the form of colorless crystals.

Melting Point=120°–121° C.

Thin-layer Chromatography (TLC): Rf=0.50 (ethyl acetate+10% diethylamine).

NMR Spectrum: $\delta = 2.5$ (m,4H) 2.7 (t,2H) 3.7 (m,4H); 4.2 (t,2H) 5.2 (s,2H mobiles); 5.7 (s,1H) 7.4 (q,4H) ppm (CDCl$_3$).

EXAMPLE 2

1-Amino-3-(p-chlorophenyl)-5-(piperidinoethoxy)-pyrazole

The process of Example 1 was repeated, using the same starting pyrazolone, but replacing the chloroethylmorpholine with chloroethylpiperidine which was added dropwise and carrying out the reaction at a temperature of 60° C. In 3 hours 1-amino-3-(p-chlorophenyl)-5-(piperidinoethoxy)-pyrazole was thus obtained. After purification as indicated in Example 1, the yield was 55%.

Melting point=119° C.

TLC Rf=0.70 (ethyl acetate+10% diethylamine).

NMR Spectrum: $\delta = 1.5$ (6H) 2.4 (4H) 2.7 (t,2H); 4.2 (t,2H); 5.3 (2H mobiles) 5.7 (s,1H); 7.4 (q,4H) ppm. (CDCl$_3$).

EXAMPLE 3

1-Amino-3-(p-chlorophenyl)-5-(piperidinopropoxy)-pyrazole

The process of Example 2 was carried out using chloropropylpiperidine in the place of chloroethylpiperidine. After extraction with citric acid then rendering alkaline with sodium carbonate as indicated in Example 1, 1-amino-3-(p-chlorophenyl)-5-(piperidinopropoxy)-pyrazole was extracted from the aqueous phase using hexane.

Melting point=90° C.

TLC Rf 0.63 (ethyl acetate+10% diethylamine).

NMR Spectrum: $\delta = 1.4$ (m,8H) 2.2 (m,6H) 4.0 (t,2H); 5.1 (s,2H mobiles) 5.5 (s,1H); 7.3 (q,4H) ppm (CDCl$_3$).

EXAMPLE 4

1-Amino-3-(p-chlorophenyl)-5-(pyrrolidinoethoxy)-pyrazole

The process of Example 1 was repeated, also starting with 1-amino-3-(p-chlorophenyl)-pyrazolone, but replacing the chloroethylmorpholine with chloroethylpyrrolidine.

After purification and extraction of the aqueous phase with diethyl ether, 1-amino-3-(p-chlorophenyl)-5-(pyrrolidinoethoxy)-pyrazole was obtained.

Melting Point=131° C.

TLC: Rf=0.50 (ethyl acetate+10% diethylamine).

NMR Spectrum: $\delta = 1.8$ (m,4H) 2.5 (m,4H) 2.9 (t,2H); 4.2 (t,2H) 5.1 (2H mobiles) 5.7 (s,1H); 7.4 (q,4H) ppm (CDCl$_3$).

EXAMPLE 5

1-Amino-3-(p-chlorophenyl)-5-[(4-phenylpiperazino)ethoxy]-pyrazole 3 g of 1-amino-3-(p-chlorophenyl)pyrazolone were dissolved in 200 ml of tetrahydrofuran. Nitrogen was bubbled into this solution then it was cooled with an ice bath and 0.45 g of potassium hydride was added. Then 6.2 g of 1-(2-chloroethyl)-4-phenylpiperazine was added progressively keeping the reaction mixture under agitation.

When the reaction was completed, the tetrahydrofuran was eliminated by distillation under reduced pressure. It was then washed and purified using the technique described in Example 1. The extraction of the aqueous alkaline phase was carried out with ethyl acetate.

After purification 3.25 g of 1-amino-3-(p-chlorophenyl)-5-[(4-phenylpiperazino)ethoxy]-pyrazole was collected.

Melting Point = 174° C.

TLC: Rf = 0.57 (ethyl acetate + 10% diethylamine).

NMR Spectrum: δ = 2.8 (m,6H) 3.2 (m,4H) 4.3 (t,2H); 4.4 (2H mobiles) 5.8 (s,1H); 6.8 to 7.7 (m,9H) ppm (CDCl$_3$).

EXAMPLE 6

1-Amino-3-phenyl-5-(pyrrolidinoethoxy)-pyrazole

The process of Example 1 was repeated, replacing the 1-amino-3-(p-chlorophenyl)pyrazolone with 1-amino-3-phenylpyrazolone, in dimethylformamide, to which chloroethylpyrrolidine in the presence of sodium hydride was added dropwise.

After purification using the technique described in Example 1, 1-amino-3-phenyl-5-(pyrrolidinoethoxy)-pyrazole was obtained.

Melting point = 138° C.

TLC: Rf = 0.70 (ethyl acetate + 10% diethylamine).

NMR Spectrum: δ = 1.8 (m,4H) 2.6 (m,6H) 2.7 (t,2H); 4.2 (t,2H) 5.1 (2H mobiles); 5.7 (s,1H) 7.1 to 7.7 (2m,5H) ppm; (CDCl$_3$).

EXAMPLE 7

1-Amino-3-phenyl-5-(morpholinoethoxy)-pyrazole

The process of Example 1 was repeated, with 1-amino-3-phenylpyrazolone as the starting material instead of 1-amino-3-(p-chlorophenyl)pyrazolone.

In this manner 1-amino-3-phenyl-5-(morpholinoethoxy)pyrazole was obtained.

Melting Point = 139° C.

TLC: Rf = 0.75 (ethyl acetate + 10% diethylamine).

NMR Spectrum: δ = 2.5 (m,4H) 2.8 (t,2H) 3.8 (m,4H); 4.2 (t,2H) 5.2 (2H mobiles); 5.7 (s,1H) 7.1 to 7.8 (2m,5H)ppm; (CDCl$_3$).

EXAMPLE 8

1-Amino-3-phenyl-4-methyl-5-(morpholinoethoxy)-pyrazole

The process of Example 1 was repeated, with 1-amino-3-phenyl-4-methylpyrazolone as the starting material instead of 1-amino-3-(p-chlorophenyl)pyrazolone.

In this manner 1-amino-3-phenyl-4-methyl-5-(morpholinoethoxy)-pyrazole was obtained.

Melting Point = 96° C.

TLC: Rf = 0.70 (ethyl acetate + 10% diethylamine).

NMR Spectrum: δ = 2.1 (s,3H) 2.5 (m,4H) 2.6 (t,2H); 3.6 (m,4H) 4.2 (t,2H) 5.4 (2H mobiles); 7.1 to 7.8 (2m,5H) ppm (CDCl$_3$).

EXAMPLE 9

1-Amino-3-phenyl-4-methyl-5-(pyrrolidinoethoxy)-pyrazole

The process of the Example 8 was repeated, adding chloroethylpyrrolidine dropwise onto the 1-amino-3-phenyl-4-methylpyrazolone, in the presence of sodium amide in tetrahydrofuran.

In this manner 1-amino-3-phenyl-4-methyl-5-(pyrrolidinoethoxy)-pyrazole was obtained.

Melting point = 109° C.

TLC: Rf = 0.70 (ethyl acetate + 10% diethylamine).

NMR Spectrum: δ = 1.7 (m,4H) 2.1 (s,3H) 2.5 (m,4H); 2.7 (t,2H); 4.2 (t,2H) 5.3 (2H mobiles) 7.1 to 7.8 (2m,5H); ppm (CDCl$_3$).

EXAMPLE 10

1-Amino-3-phenyl-5-[(dimethylamino)ethoxy]-pyrazole

The process of Example 1 was repeated, adding N-chloroethyl-dimethylamine dropwise to the 1-amino-3-phenylpyrazolone, in dimethylformamide, in the presence of sodium hydride.

In this manner 1-amino-3-phenyl-5-[(dimethylamino)ethoxy]-pyrazole was obtained.

Melting Point = 80° C.

TLC: Rf = 0.75 (ethyl acetate + 10% diethylamine).

NMR Spectrum: δ = 2.2 (s,6H) 2.6 (t,2H) 4.0 (t,2H); 5.3 (2H mobiles), 5.6 (s,1H); 7.1 to 7.7 (2m,5H) ppm (CDCl$_3$).

The aminoalkoxy pyrazoles of the general formula (I) of the present invention have interesting pharmacological properties enabling their application to be envisaged in therapy.

Toxicological assays have enabled the determination, for the derivatives of the general formula (I) described in Examples 1 to 10 above, of a lethal dose LD$_{50}$ of generally between 500 and 1,000 mg/kg.

The aminoalkoxypyrazoles of the invention have an antidepressive activity comparable to that of tricyclic antidepressants and amphetamines, but they act differently. This activity has been verified on stereotypies induced by 5-hydroxytryptophane, a precursor of serotonin. In this test, it was noticed that the aminoalkoxypyrazoles increase the stereotypies but hinder hypothermia.

This antidepressive activity was confirmed by verification of practically total anticataleptic activity at the level of catalepsy induced by a neuroleptic (chlorpromazine).

Tests on convulsions induced by pentatetrazole and electroshock showed very definite anticonvulsive activity.

Finally, the aminoalkoxypyrazoles of the invention have cardiovascular activity, manifesting itself by strong cardiac depressant activity, an effect of slowing cardiac frequency without lessening the pressure or the force of the contractions, antiarrhythmic properties and an important spasmolytic action.

These properties show that the aminoalkoxypyrazoles of the general formula (I) of the invention can be used in human or veterinary medicine, in particular for treatment of depressive states and cardiac disorders.

The aminoalkoxypyrazoles of the invention can be administered in the forms conventional in the art, for example, in the form of tablets, pills, capsules, lozenges, suppositories, injectable solutions or syrups, the active constituent being diluted in an appropriately selected pharmaceutically acceptable carrier or diluent.

Dosage may vary according to the subject being treated and the disorder in question. Doses administered daily are generally between 5 and 200 mg for oral administration in man.

While the invention has been described in detail and with reference to specific embodiments thereof, it will be apparent to one skilled in the art that various changes and modifications can be made therein without departing from the spirit and scope thereof.

What is claimed is:

1. An aminoalkoxypyrazole of the general formula (I)

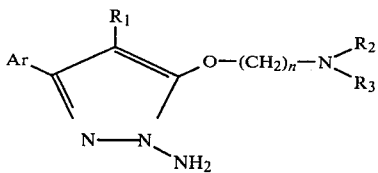

(I)

wherein Ar is a phenyl, benzyl or naphthyl group, or a phenyl group substituted by one or more halogen atoms, or by one or more alkyl, cyano, nitro, hydroxy or alkoxy groups; $R_1$ is a hydrogen atom or an alkyl group; $R_2$ and $R_3$, which may be the same or different, are a hydrogen atom or an alkyl group, or form, with the nitrogen atom to which they are attached, a 5- to 7-membered heterocyclic ring; n is an integer of from 1 to 4; as well as the mineral or organic acid salts thereof.

2. The aminoalkoxypyrazole of claim 1, wherein Ar is a phenyl group, or a phenyl group substituted by one or more halogen atoms.

3. The aminoalkoxypyrazole of claim 2, wherein Ar is a phenyl group or a p-chlorophenyl group.

4. The aminoalkoxypyrazole of claim 1, 2 or 3, wherein $R_2$ and $R_3$ are a methyl group, or form, with the nitrogen atom to which they are attached, a pyrrolyl, pyrrolidinyl, pyrrolinyl, piperidyl, morpholinyl or piperazinyl group, said groups being unsubstituted or substituted with an alkyl group or a phenyl group.

5. The aminoalkoxypyrazole of claim 1, selected from the group consisting of:

1-amino-3-(p-chlorophenyl)-5-(morpholinoethoxy)-pyrazole,
1-amino-3-(p-chlorophenyl)-5-(piperidinoethoxy)-pyrazole,
1-amino-3-(p-chlorophenyl)-5-piperidinopropoxy)-pyrazole,
1-amino-3-(p-chlorophenyl)-5-(pyrrolidinoethoxy)-pyrazole,
1-amino-3-(p-chlorophenyl)-5-[(4-phenyl-piperazino)ethoxy]-pyrazole,
1-amino-3-phenyl-5-(pyrrolidinoethoxy)-pyrazole,
1-amino-3-phenyl-5-(morpholinoethoxy)-pyrazole,
1-amino-3-phenyl-4-methyl-5-(morpholinoethoxy)-pyrazole,
1-amino-3-phenyl-4-methyl-5-(pyrrolidinoethoxy)-pyrazole,
1-amino-3-phenyl-5-[(dimethylamino)ethoxy]-pyrazole.

6. A medicinal composition for the treatment of cardiac disorders or depressive states comprising a therapeutically effective amount of an aminoalkoxypyrazole of claim 1, 2 or 3 or a pharmaceutically acceptable salt thereof along with a pharmaceutically acceptable carrier or diluent.

7. A medicinal composition for the treatment of cardiac disorders or depressive states comprising a therapeutically effective amount of an aminoalkyoxypyrazole of claim 4 or a pharmaceutically acceptable salt thereof along with a pharmaceutically acceptable carrier or diluent.

8. A medicinal composition for the treatment of cardiac disorders or depressive states, comprising a therapeutically effective amount of an aminoalkoxypyrazole of claim 5 or a pharmaceutically acceptable salt thereof along with a pharmaceutically acceptable carrier or diluent.

* * * * *